United States Patent [19]

Weis et al.

[11] Patent Number: 4,950,819

[45] Date of Patent: Aug. 21, 1990

[54] PROCESS FOR THE PREPARATION OF ALKALI METAL SALTS OF PHOSPHONIC ACID MONOALKYL ESTERS

[75] Inventors: Claus D. Weis, Pfeffingen; Peter Sutter, Muttenz, both of Switzerland

[73] Assignee: Ciba-Geigy Corporation, Ardsley, N.Y.

[21] Appl. No.: 245,489

[22] Filed: Sep. 19, 1988

[30] Foreign Application Priority Data

Oct. 1, 1987 [CH] Switzerland ............... 3824/87

[51] Int. Cl.$^5$ .................................. C07F 9/40
[52] U.S. Cl. .................................. 558/131
[58] Field of Search .......................... 558/131

[56] References Cited

U.S. PATENT DOCUMENTS 2,951,086  8/1960  Chadwick ........................... 558/131
3,524,846  8/1970  Moffatt et al. ..................... 558/131
4,043,794  8/1977  Sauers .............................. 558/131

OTHER PUBLICATIONS

Inorganica Chimica Acta 3, 523–526 (1969), C. M. Mikulski et al.
Journal of the Indian Chemistry Society, XLIX (49), 77–81 (1972), D. M. Puri.
Abramov et al, "Zhur Obsch Khim" (English Translation), vol. 22, (1959), pp. 971–977.

Christal et al, "Jou. Organo Metal Chem.," (1968) vol. 12, pp. 459–470.

Primary Examiner—Anton H. Sutto
Attorney, Agent, or Firm—Kevin T. Mansfield; Edward McC. Roberts

[57] ABSTRACT

A process for the preparation of alkali metal salts of phosphonic acid monoalkyl esters of formula

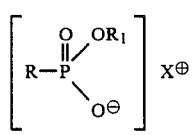 (1)

by reacting 1 mole of a phosphonic acid ester of formula

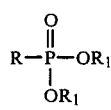 (2)

with 1 mole of a finely particulate alkali metal halide of formula XY. In these formulae, R is straight chain or branched $C_1$-$C_{20}$alkyl, $R_1$ is $C_1$-$C_4$alkyl, X is an alkali metal cation and Y is a halogen anion.

5 Claims, No Drawings

PROCESS FOR THE PREPARATION OF ALKALI METAL SALTS OF PHOSPHONIC ACID MONOALKYL ESTERS

The present invention relates to a novel process for the preparation of alkali metal salts of phosphonic acid monoalkyl esters.

The preparation of the sodium salt of monomethyl methylphosphonate by partial alkaline hydrolysis of dimethyl methylphosphonate in water, or a mixture of dioxane/water, with aqueous sodium hydroxide has been described by H. Cristol, M. Levy and C. Marty in J. Organometallic Chem. 12, 495 (1968).

A process has now been found in which alkali metal salts of phosphonic acid monoalkyl esters can be prepared in simple and economic manner.

The process of this invention for the preparation of alkali metal salts of phosphonic acid monalkyl esters of formula

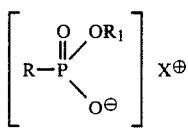 (1)

wherein
R is straight chain or branched $C_1$–$C_{20}$alkyl,
$R_1$ is $C_1$–$C_4$alkyl, and
X is an alkali metal cation,
comprises reacting 1 mole of a phosphonic acid ester of formula

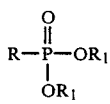 (2)

wherein R and $R_1$ are as defined above, with 1 mole of a finely particulate alkali metal halide of formula

XY (3)

wherein
X is an alkali metal cation, and
Y is a halogen anion,
in the temperature range from 30° to 220° C.

The alkali metal halides employed in this reaction must be in finely particulate form. This is achieved by grinding the alkali metal halides in a ball mill to an average particle size of 30–50 .

The reaction with the alkali metal halide is preferably carried out in the temperature range from 50° to 180° C., depending on the halide employed.

A preferred process comprises reacting a phosphonic acid ester of formula (2), wherein R is $C_1$–$C_4$alkyl, with an alkali metal halide of formula (3), wherein X is lithium, sodium or potassium, and Y is chlorine, bromine or iodine.

The preferred alkali metal halides are sodium and potassium chloride.

A particularly preferred process comprises reacting a phosphonic acid ester of formula (2), wherein R and $R_1$ are methyl, with sodium chloride. The methyl chloride so obtained can then be used as industrial methylating agent.

In the process of this invention it is advantageous to use a 5 to 60%, preferably a 20 to 50%, excess of the phosphonic acid ester when using a potassium or sodium halide.

Alkali metal salts of formula (1), wherein R is straight chain or branched unsubstituted $C_1$–$C_{20}$alkyl and $R_1$ is $C_1$–$C_4$alkyl, are useful emulsifiers for aqueous plastics dispersions (q.v. for example U.S. Pat. No. 4,233,198), and those wherein R and $R_1$ are $C_1$–$C_4$alkyl are used as flame retardants.

Alkali metal salts of formula (1), wherein R is $C_1$–$C_7$alkyl and $R_1$ is hydrogen, methyl or ethyl, are disclosed in U.S. Pat. No. 4,251,492. These salts are used as complexing agents in solutions for removing $H_2S$ from gases or liquid hydrocarbons.

The process of this invention is illustrated by the following Examples in which percentages are by weight, unless otherwise stated.

EXAMPLE 1

With stirring, 11.6 g of finely powdered sodium chloride are dispersed in 80 ml of dimethyl methylphosphonate and the dispersion is heated for 50 minutes to reflux, with stirring. Methyl chloride evolving during the reaction is drawn off and excess dimethyl methylphosphonate is removed by distillation under a low vacuum, affording 26.6 g (theory: 26.4 g) of a crystalline residue to which 30 ml of toluene are added. The resultant salt is isolated by filtration and dried under vaccum at 100° C., to give 26 g (98% of theory) of the sodium of formula

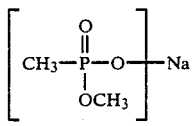

which melts at 315°–320° C.

EXAMPLE 2

With stirring, 5.9 g of finely powdered sodium chloride are dispersed in 80 ml of diethyl methylphosphonate and the dispersion is heated for 2 hours to 180° C., with stirring. The clear, colourless solution is concentrated under reduced pressure (26 mbar) on a rotary evaporator. The white crystalline residue is dissolved in 120 ml of hot methanol and insoluble matter is removed by filtration. The filtrate is evaporated to dryness and the white residue is stirred in 50 ml of a 1:1 mixture of diethyl ether/acetone, filtered and dried, affording 12.25 g (84% of theory) of the sodium salt of formula

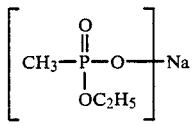

which melts at 183°–186° C.

EXAMPLE 3

With stirring, 7.45 g of finely powdered potassium chloride are dispersed in 150 ml of dimethyl methylphosphonate and the dispersion is heated for 60 minutes to weak reflux. The evolution of methyl chloride ceases after this time. Excess dimethyl methylphosphonate is distilled off under a low vacuum and the residue is stirred for 5 minutes in a mixture of 30 ml of acetone and 30 ml of diethyl ether. The dispersion is filtered, affording 10.4 g (70% of theory) of the potassium salt of formula

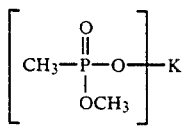

which melts at 215°–218° C.

EXAMPLE 4

With stirring, 8.48 g of finely ground lithium chloride are dispersed in 300 ml of dimethyl methylphosphonate and the dispersion is heated for 60 minutes to reflux, with stirring. Excess dimethyl methylphosphonate is then distilled off under a low vacuum on a rotary evaporator and the residue is evaporated to dryness. The white crystals are stirred in 150 ml of diethyl ether, isolate by filtration and washed on the filter with 100 ml of diethyl ether and then freed from solvent under vacuum, to give 17.7 g (76% of theory) of the lithium salt formula

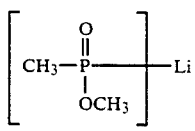

which melts at >300° C.

EXAMPLE 5

With stirring, 16.75 g of finely ground lithium iodide are dispersed in 150 ml of dimethyl methylphosphonate and the dispersion is heated for 1 hour to 120° C., with stirring. The white suspension is then evaporated to dryness under reduced pressure on a rotary evaporator and to the residue are added 50 ml of a 1:1 mixture of acetone/diethyl ether. The residual crystals are isolated by filtration and dried under vacuum at 100° C., to give 5.5 g of the lithium salt of formula

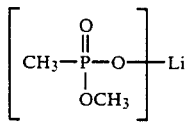

which melts at >300° C.

EXAMPLE 6

With stirring, 4.24 g of finely ground lithium chloride are dispersed in 80 ml of diethyl methylphosphonate and the dispersion is heated for 30 minutes of reflux, with stirring. When the evolution of gas has ceased, the diethyl methylphosphonate is distilled off under a low vacuum. To the white crystalline residue are added 50 of a 1:1 mixture of diethyl ether/acetone. The residual crystals are isolated by filtration, to give 7.8 g (60% of theory) of the lithium salt of formula

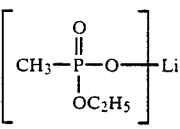

which melts at >300° C.

EXAMPLE 7

With stirring, 17.4 g of finely ground lithium bromide are dispersed in 300 ml of dimethyl methylphosphonate and the dispersion is heated for 1 hour to 160° C., with stirring. Excess dimethyl methyl phosphonate is distilled off under a low vacuum on a rotary evaporator. The residue is stirred for 5 minutes in 300 ml of a 1:1 mixture of acetone/dimethyl ether. The dispersion is then filtered and the filter residue is washed with 50 ml of a 1:1 mixture of acetone/dimethyl ether, to give 20.2 g (87.5% of theory) of lithium salt of formula

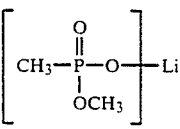

which melts at >300° C.

EXAMPLE 8

With stirring, 20.6 g of finely ground sodium bromide are dispersed in 300 ml of dimethyl methylphosphonate and the dispersion is heated for 1 hour to the boil, with stirring. Excess dimethyl methylphosphonate is then distilled off under a low vacuum (26 mbar) at 110° C. The crystalline residue is stirred in a mixture of 70 ml of acetone and 30 ml of diethyl ether and the crystals are thereafter isolated by filtration and dried, to give 18.6 g (70.5% of theory) of the sodium salt of formula

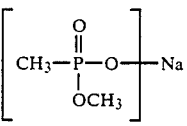

which melts at 315°–320° C.

EXAMPLE 9

With stirring, 11.6 g of finely ground sodium chloride are dispersed in 80 ml of diethyl ethylphosphonate and the dispersion is heated for 3 hours to 220° C., with stirring. Excess diethyl ethylphosphonate is then distilled off on a rotary evaporator. The residual oil crystallises over the course of 4 weeks. The crystals are stirred twice in a 3:1 mixture of acetone/diethyl ether, isolated by filtration and then washed with 50 ml of acetone. The solvent is removed under vacuum, to give 27 g (84% of theory) of the sodium salt of formula

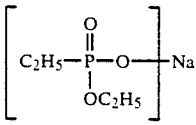

What is claimed is:

1. A process for the preparation of an alkali metal salt of a phosphonic acid monoalkyl ester of the formula

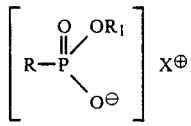 (1)

wherein

R is a straight chain or branched $C_1$-$C_{20}$alkyl, $R_1$ is $C_1$-$C_4$alkyl, and X is an alkali metal cation, which comprises reacting 1 mole of a phosphonic acid ester of the formula

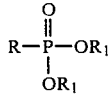 (2)

wherein R and $R_1$ are as defined above, with 1 mole of a finely particulate alkali metal halide of the formula

XY  (3)

wherein

X is an alkali metal cation and

Y is a halogen anion, in a temperature range from 30° to 220° C., for 30 minutes to 3 hours in the absence of a solvent.

2. A process according to claim 1, wherein R is $C_1$-$C_4$alkyl, X is lithium, sodium or potassium, and Y is chlorine, bromine or iodine.

3. A process according to claim 1, wherein the reaction is carried out in the temperature range from 50° to 180° C.

4. A process according to claim 2, wherein X is sodium or potassium and Y is chlorine.

5. A process according to claim 4, wherein a 5 to 60% excess of the phosphonic acid ester is used.